United States Patent
Niedhart et al.

(10) Patent No.: US 6,818,332 B1
(45) Date of Patent: Nov. 16, 2004

(54) BIOACTIVE IMPLANTS AND METHOD FOR THE PRODUCTION THEREOF

(76) Inventors: Christopher Niedhart, Elsa-Brandstöm-Strasse 16, 52070 Aachen (DE); Hans-Michael Sax, Walhorner Strasse 3, 52074 Aachen (DE); Fritz Uwe Niethard, 2 Rote-Haaq-Weg 32d, 52076 Aachen (DE); Rainer Telle, Clermontstrasse 51, 52068 Aachen (DE)

(*) Notice: Subject to any disclaimer, the term of this patent is extended or adjusted under 35 U.S.C. 154(b) by 0 days.

(21) Appl. No.: 09/857,972
(22) PCT Filed: Dec. 17, 1999
(86) PCT No.: PCT/EP99/10091

§ 371 (c)(1),
(2), (4) Date: Jun. 13, 2001

(87) PCT Pub. No.: WO00/37121
PCT Pub. Date: Jun. 29, 2000

(30) Foreign Application Priority Data

Dec. 17, 1999 (DE) ................................ 198 58 501

(51) Int. Cl.$^7$ ................................................ B32B 9/00
(52) U.S. Cl. .................. 428/702; 423/11.11; 423/11.16
(58) Field of Search ............................... 428/689, 702; 623/11.11, 16.11, 919, 923; 427/2.24, 2.26, 2.27

(56) References Cited

U.S. PATENT DOCUMENTS 4,652,459 A * 3/1987 Engelhardt ............ 128/DIG. 21
4,950,294 A      8/1990 Hakamatsuka
6,121,172 A * 9/2000 Marcolongo et al. ........ 442/301

FOREIGN PATENT DOCUMENTS

| DE | 29 10 335   | 10/1979 |
| DE | 29 54 180   | 10/1979 |
| DE | 39 02 951   | 8/1989  |
| DE | 39 14 999   | 9/1990  |
| DE | 40 32 570   | 4/1992  |
| DE | 197 44 809  | 7/1999  |
| EP | 0 864 332   | 9/1998  |
| WO | WO 94/04657 | 3/1994  |

OTHER PUBLICATIONS

Willmann, G., et al., "Improvement of the Safety of Ceramic Femoral Heads for Total Hip Replacement". Biomedizinische Technik: 40, 342–346, Dec., 1995. Abstract Only.

* cited by examiner

Primary Examiner—Deborah Jones
Assistant Examiner—Arden Sperty
(74) Attorney, Agent, or Firm—Nath & Associates PLLC; Gary M. Nath; Jerald L. Meyer

(57) ABSTRACT

The invention relates to an implant which is provided for the human or animal body and which at least partially consists of ceramic, glass or glass-ceramic material. The inventive implant comprises hydroxide compounds on the surface thereof which are formed from the oxide compounds of the ceramic, glass or of the glass-ceramic material. The implants can be produced, in particular, using a lye treatment.

13 Claims, 5 Drawing Sheets

BIOACTIVE IMPLANTS AND METHOD FOR THE PRODUCTION THEREOF

This application is The National Stage of the International Application No. PCT/EP99/10091 filed Dec. 19, 1999.

The invention relates to bioactive implants and processes for production of implants for use in the human or animal body and in particular implants which consist at least partly of ceramic, glass or glass ceramic, produced in the shape to be used later.

DESCRIPTION OF THE RELATED ART

Implants known and employed in medical technology are used particularly in the form of prostheses or bone replacement materials in the orthopaedic and dental prosthetic field. Metals, plastics and inorganic-non-metallic materials (glass, ceramic and binders) and material composites of the aforementioned groups of materials, are thus used. The most well-known example of bioceramics is thus the hip-joint head made from aluminium oxide-ceramic. Such implants are produced from aluminium oxide powder via a powder-metallurgical route. The synthetic raw material is worked up, pressed isostatically, processed while "green" or "white", that is in the pressed or prefired state, then sintered, resintered heat-isostatically and then hard-processed to grind and polish.

The known implants made from pure hard ceramics, such as for example aluminium oxide, show the best abrasion strength, which is of considerable importance particularly for use as joint prostheses, for example for artificial hip joints. However, prostheses made from pure aluminium oxide have not been successful in practice, since the early loosening rate is very large. This can be attributed to the fact that aluminium oxide ceramic is bioinert, that is that active growth of the body tissue into or onto the implant does not take place, but that there is formation of a fibrous-tissue intermediate layer. This leads to proper retreat of the body tissue particularly in zones in which particular stresses of the implant act on the surrounding tissue, so that the stress peaks are displaced into other regions, where likewise retreat of the tissue then takes place.

Bioactive materials, such as for example hydroxylapatite or tricalcium phosphate, show good inward growth/onward growth of the bone, but are not stable to stress and are therefore not suitable for prosthetics and only to a limited extent as bone replacement material. Implants and production processes relating to them, which consist of the material combinations metal-polyethylene, metal-metal or ceramic-ceramic, are known from the state of the art. Ceramic-ceramic combinations thus clearly show the best abrasion strength. Pure aluminium oxide ceramics are not used due to the bioinertness of the ceramics made from aluminium oxide used hitherto and the high early loosening rate resulting therefrom. However, implants and production processes relating to them are known which consist of a combination of ceramic for the gliding surface and metal alloys for the tissue contact. Suitable metals are, in particular titanium and cobalt-chromium-molybdenum alloys. From the point of view of materials technology, such a material combination has the advantage that, particularly for mechanically highly-stressed prostheses, the base body of the implant having bone contact may consist of a ductile metal and the part exerting the hinge function (head or socket) may consist of a particularly abrasion-resistant hard ceramic. The ceramic constituents may be placed, for example on the metallic base body. Although the metals or metal alloys used are also bioinert, service lives of about 10 to 15 years can be achieved using the implants described above. However, at the latest even for these implants, the loosening process is then so far advanced that the ability to function, for example of a hip-joint prosthesis, is acutely endangered. Implants likewise conventional in the state of the art, which are produced purely from metal, show comparable loosening behaviour. In addition to the still unsatisfactory fatigue durability, they additionally have a less favourable abrasion strength than implants made from hard ceramics.

In order to improve the bioactivity of the known implants, it has been proposed recently to coat the surface of the implants consisting of bioinert material with hydroxylapatite ceramic. For this purpose, hydroxylapatite layers of about 100 to 200 $\mu$m thickness are usually applied by means of a plasma-spraying process—in particular to the most stressed regions of the prosthesis. The setting of the bone onto the prosthesis should be improved with the aid of such a bioactive surface and hence a more intimate bone-implant contact should be provided. Since such coating processes have only been used for a short time, long-term results are still lacking. The early results with such prostheses are however encouraging. It is to be regarded as disadvantageous in the aforementioned coating process that the hydroxylapatite layer may peel off under extreme stresses, since base material and coating material have different stiffnesses and material properties. A further disadvantage of such implants is their high price which is due to the complicated production.

The object of the invention is to provide implants which on the one hand can be highly mechanically stressed and have good abrasion strength, are characterised on the other hand by good onward growth behaviour regarding the body tissue and which can be produced in simple and cost-effective manner, particularly also for use for prostheses. The aim is the provision of bioactive implants and implant materials which can be highly mechanically stressed.

BRIEF SUMMARY OF THE INVENTION

Accordingly, the object of the invention is an implant, which consists at least partly of ceramic, glass or glass ceramic in a shape to be used later for the human or animal body and which has hydroxide compounds formed by reaction from oxide compounds of the ceramic, glass or glass ceramic, which are close to the surface, at least on part of its ceramic, glass and/or glass ceramic surface. According to the invention, in these oxide-ceramic implants, at least some of the oxide compounds are converted to hydroxide compounds at least on a part of the ceramic, glass or glass-ceramic surface. This leads to increased adhesion rate and proliferation of cells, for example osteoblasts, on the surface of an implant thus produced. The long-term stability may be significantly increased by the improved onward growth behaviour. In fact, such an implant is characterised, even when using only ceramic, glass or glass ceramic, that is all bioinert materials, by an increased primary adhesion of target cells (in particular osteoblasts) due to the hydroxide compounds produced on the surface thereof. This leads to a significantly improved long-term wearing time of such implants, for example when used as joint prostheses, but also in the dental field and in the field of orthopaedics. This applies particularly to implants made from aluminium oxide ceramic. It is advantageous that the hydroxide compounds are already formed on a surface which has a shape as is intended for the later use of the implant. Implants of different bioactivity for use in the human and animal body are thus available due to differences in the density and the type of hydroxide compounds preformed on the surface. The invention thus makes implants accessible to a considerable bioactivity bandwidth. The implants of the invention may carry biocompatible substances which are coupled to modified surfaces.

The object of the invention is also a process for producing an implant, which consists at least partly of ceramic, glass or glass ceramic, for use in the human or animal body, wherein at least part of the surface of the implant, which has ceramic, glass or glass ceramic, is exposed to a lye. At least part of this oxide ceramic treated with lye is advantageously present in the shape to be used later.

Pure ceramic implants, which show good bioactive behaviour with high long-lasting stress stability and hence good implant contact, can be realised with the aid of the process of the invention. Depending on the type and concentration of the lye used and the action temperature and duration, "bioactivation" of different strength can be achieved. In the process according to the invention, a new layer of a foreign material is not applied, as for the known plasma-hydroxylapatite coating, but rather oxide compounds of the implant containing glass, ceramic or glass ceramic, which are close to the surface, are converted to form hydroxide compounds by a reaction. The layer thickness of the activated layer firmly anchored to the substrate obtained by an at least partial conversion of the surface of the substrate is extremely thin and completely adequate for achieving the aim, namely improvement of the onward growth behaviour. The danger of peeling-off of a layer having material properties deviating from the base body, that is from the ceramic, glass or glass ceramic, does not exist.

According to one embodiment of the invention, provision is made in that the lye and/or the surfaces of the implant to be treated during the treatment has a temperature above 50° C., preferably between 80° C. and 120° C. The period of action with respect to lower lye temperatures may be shortened in this manner.

Accelerated formation of the hydroxide compounds can also be achieved by lye treatment taking place under a pressure which is increased compared to the atmospheric pressure.

The process of the invention can be carried out particularly simply if the implant is immersed at least partly in a bath of the lye.

A particularly advantageous embodiment of the process consists in that the implant consists of aluminium oxide ceramic and the lye is a 30% strength sodium hydroxide solution. Lyes, such as for example sodium hydroxide solution and other strong, for example inorganic lyes, may also generally be used as the lye in high aqueous concentrations.

An advantageous embodiment lies in the fact that surface regions of the implant and/or the lye near the surface regions of the implant to be treated are locally heated. Implants—starting from a treatment with a moreover, comparatively cold lye—having locally different strength bioactivity, may be realised using such a procedure. Such an implant is particularly useful if the onward growth behaviour is to be particularly promoted in certain regions, whereas other regions are to remain as bioinert as possible.

Particularly exact metering and spatial distribution of the hydroxylated surface regions can be realised if the treatment with lye is assisted by pulsed laser radiation.

A further development of the process of the invention consists finally also in that bioactive substances are coupled at least to part regions of the surface regions of the implant exposed to a lye. The bioactive substances may be, for example whole proteins, for example fibronectin, or peptide sequences, for example RGD binding sequences, or active groups of osteoinductive materials, for example BMP. Suitable materials to be coupled are also, for example calcium phosphates or special materials. Specific control of the osseous inward growth behaviour is possible in the aforementioned manner.

The implant according to the invention can be produced in simple manner and more cost-effectively than the implant according to the state of the art. Compared to composite implants or material combinations, such as hard ceramic and metal or implants coated with hydroxylapatite, the production costs are even significantly lower. Very good results can be achieved, for example if the implant consists of aluminium oxide ceramic and is treated with sodium hydroxide solution.

The invention is illustrated in more detail below using an exemplary embodiment in the form of the production of an implant.

DETAILED DESCRIPTION OF THE INVENTION

A slip, which is digested for a period of about 24 hours on the roller bench, is prepared from a ceramic aluminium oxide powder permitted for clinical use while adding polyvinyl alcohol as binder and polycarboxylic acid as liquifier. The weight portion of the binder is 2%, that of the liquifier 0.3%, in each case based on the dry substance. The ratio of deionised water to solid is 35:65.

Following liquidification, before spray-drying, a defoamer is added, the weight portion of which is 0.05%. A green compact of the particular implant is subsequently produced using suitable pressing moulds. The pressing pressure thus applied is about 100 MPa. The subsequent ceramic firing takes place in a muffled firing oven. Debindering of the organic auxiliaries takes place at 500° C. for about 2 hours, the actual ceramic firing at about 1,600° C. likewise for 2 hours. The temperature gradient, starting from the room temperature to the debindering temperature, from the debindering temperature to the sintering temperature and from the sintering temperature back to room temperature is between 2 and 3 K/minute.

The sintered implants may be introduced without further surface processing directly into a flask, in which the sodium hydroxide solution used for treatment is situated. The flask used is made from polytetrafluoroethylene (PTFE) or polytetrafluoroacrylate (PTFA) plastic for reasons relating to anti-corrosion. The 30% strength sodium hydroxide solution (30 wt. %) used is heated with the aid of a heating mantle to a temperature between 90 and 110° C. Continuous operation of the device is achieved with the aid of a reflux condenser due to recovery of the liquid medium. Depending on the required degree of activation, the lye treatment of the selected implant surface takes place at atmospheric pressure for a period of time of between 12 and 96 hours.

Figure 1:
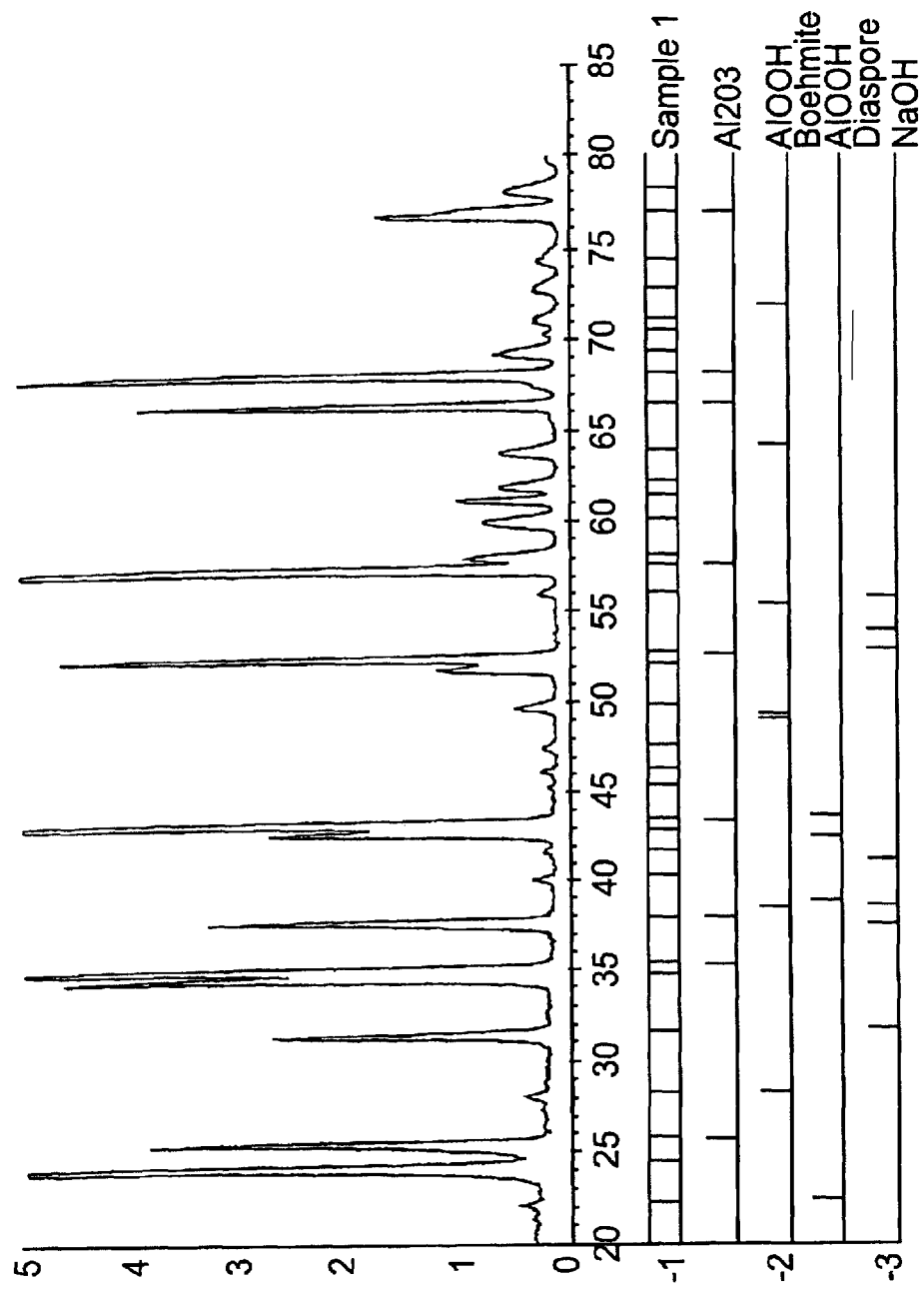
FIG. 1 shows a phase diagram of the surface regions of an activated aluminium oxide implant of the invention, recorded by means of small-angle X-ray diffraction.

The aluminium oxide implants produced in this manner are phase-pure. As can be seen from FIG. 1, conversion of aluminium oxide into aluminium hydroxides on the implant surfaces can be observed by means of small-angle X-ray diffraction. The mineral phases designated as diaspore and boehmite thus occur, the hydroxyl groups of which are responsible for the bioactive material behaviour.

Figure 2:
FIG. 2 shows the target cells made visible by AP colouration on the surface of an implant according to the state of the art.
Figure 3:
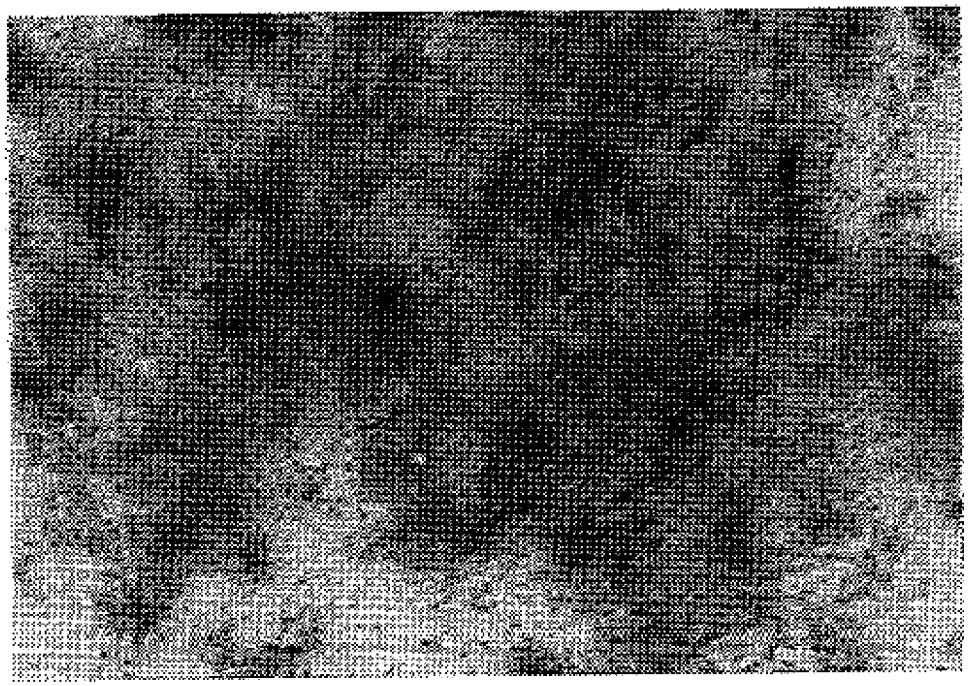
FIG. 3, like FIG. 2, but for an implant of the invention, the surface of which has been exposed beforehand to a lye.

A comparison of the different onward growth behaviour of an implant made from untreated pure aluminium oxide ceramic and an implant of the invention, the surface of which has been treated with sodium hydroxide solution, is possible using FIGS. 2 and 3, in which there is a 40-times enlargement. Adhered osteoblasts can thus be recognised on the ceramic using the alkaline phosphatase colouration (dark). Individual cells are coloured in FIG. 2 (traditional $Al_2O_3$ ceramic). The cell number of AP-positive cells is increased in FIG. 3 (implant of the invention having bioactive surface) and so-called "clusters" (AP-positive cell masses) are formed, later mineralisation centres, as proof of advanced cell differentiation. This verifies the very high bioactivity of the implant of the invention.

Figure 4:
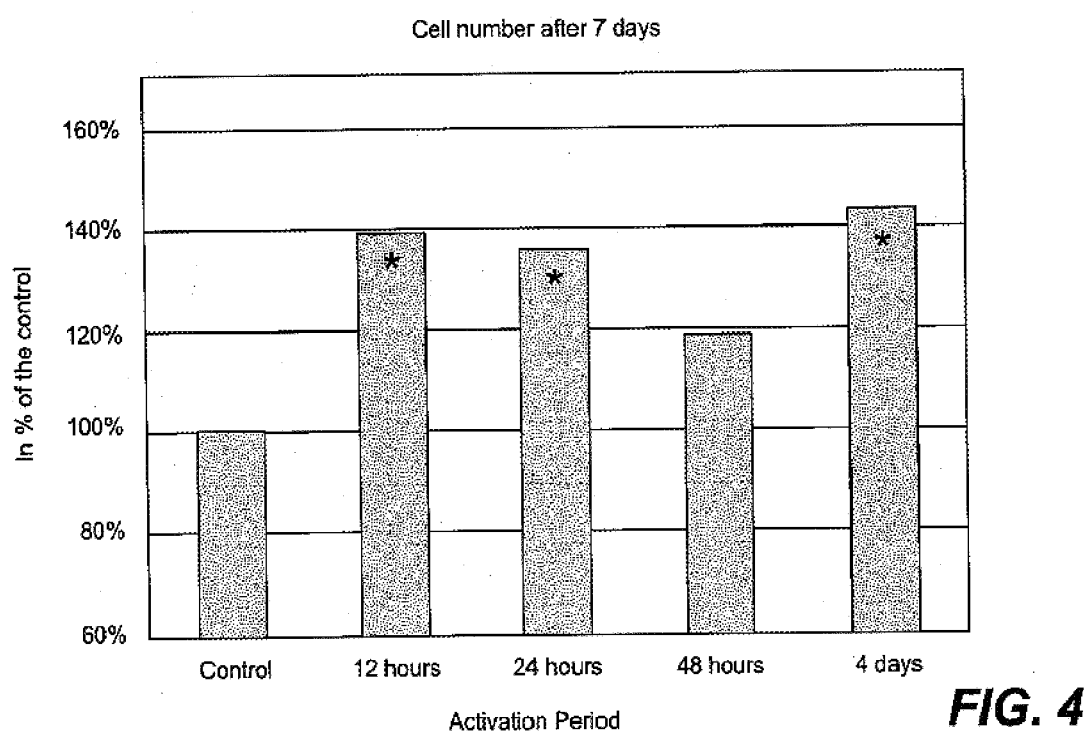
FIG. 4 shows a histogram with the dependence of the cell number on the activation period.

FIG. 4 shows the adhesion rate of human osteoblasts on implant of the invention compared to untreated control ceramic as a function of the activation period in NaOH (12 hours to 4 days) after 7 days in culture. There are 20–45% more cells on the implant of the invention than on the untreated ceramic (control). The difference to the control is statistically significant at $p<0.05$ for the samples characterised by *.

The procedure of the invention can be carried out not only for mouldings used later as a typical implant, but also for those mere carrier bodies consisting of the same starting materials (ceramic, glass, glass ceramic) which may then serve as starting base for artificial organs by specific coupling of bioactive substances.

Human osteoblasts have been taken from removed hip heads by explant technology. For this the bone was comminuted and placed in Petri dishes in 1 mm_size pieces. Cultivation takes place in Dulbecco's DMEM medium with addition of 10% calf serum and 1% penicillin/streptomycin. After three weeks, the confluently fully developed cells were subject to passages, after a further two weeks and renewed subjecting to passages, the dissemination of $4\times10^4$ cells on test bodies (22 mm diameter) took place. Adhesion was checked after 24 hours, cytotoxicity and protein secretion/mineralisation after 7 days.

Signs of cytotoxicity or growth inhibition were not found. Cell adhesion was increased to a maximum 120% ($p<0.05$) compared to the untreated test bodies after 24, 48 and 96 hours of activation time. The alkaline phosphatase secretion as a sign of differentiation was significantly increased to a maximum 130% with respect to the control after 24 and 48 hours activation time. There were no differences with regard to oesteocalcin secretion, mineralisation could be detected on all samples.

Figure 5:
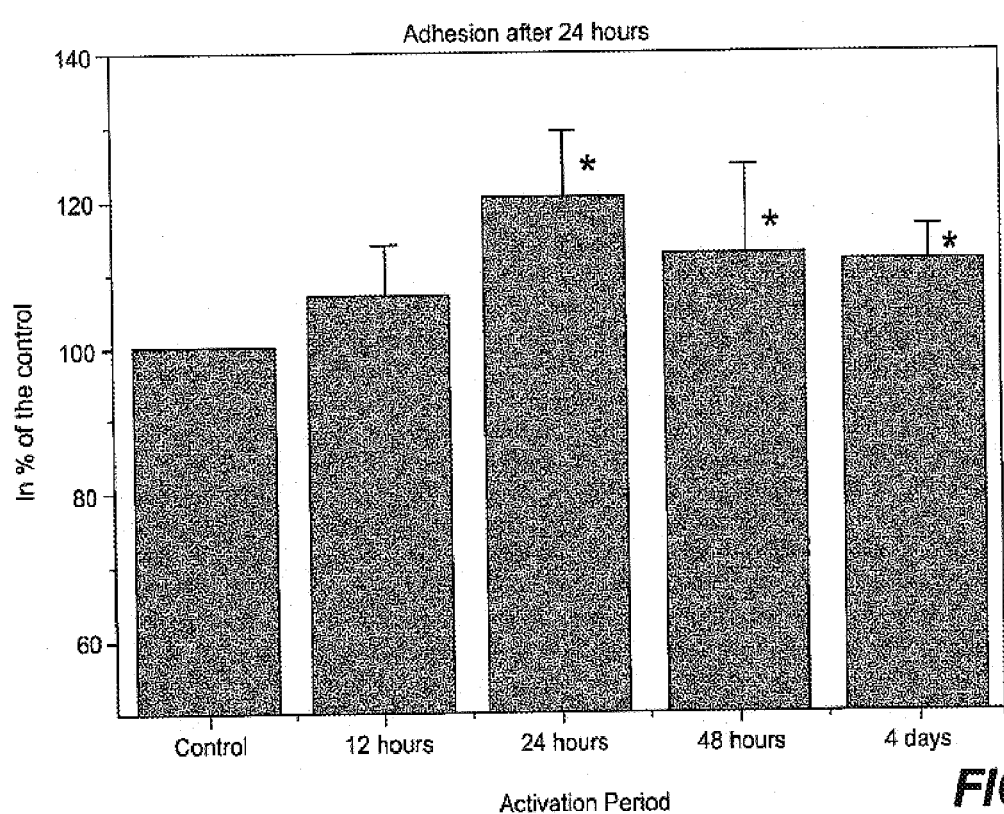
FIG. 5 shows a histogram with the dependence of adhesion on the activation period.
Figure 6:
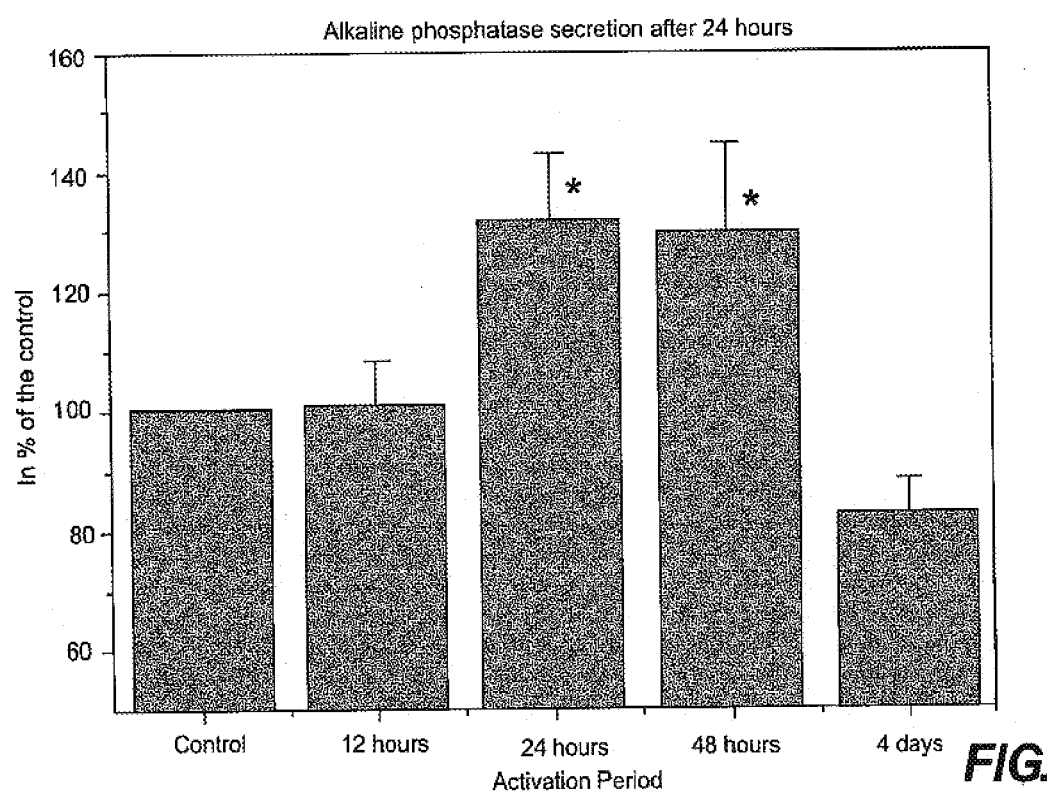
FIG. 6 shows a histogram with the dependence of phosphatase secretion on the activation period.

Bioactivation of bioinert oxide ceramics can be proved unambiguously with the aid of these results also shown graphically in FIGS. 5 and 6. Average value and standard error from six tests, expressed in per cent of the control, are shown.

What is claimed is:

1. An implant for an animal, comprising: an implant constructed at least partly of aluminum oxide ceramic, wherein said implant has hydroxide compounds formed from oxide compounds at least on part of the ceramic surface.

2. Implant according to patent claim 1, wherein said hydroxide compounds are formed from aluminum oxide.

3. Implant according to patent claim 1, characterised in that biocompatible substances are coupled to the surface hydroxide compounds.

4. A process for producing an implant for use in an animal comprising the steps of, providing an implant constructed at least partly of aluminum oxide ceramic, wherein at least part of the surface of the implant is exposed to a lye.

5. Process according to patent claim 4, characterized in that a temperature of the lye and/or of the implant surfaces to be treated is greater than 50° C.

6. Process according to claim 4, characterised in that the lye treatment takes place under a pressure which is increased compared to atmospheric pressure.

7. Process according to claim 4, characterised in that the implant is immersed at least partly in a bath of the lye.

8. Process according to claim 4, characterised in that the implant consists of aluminium oxide ceramic and the lye is 30% strength sodium hydroxide solution.

9. Process according to claim 4, characterised in that surface regions of the implant to be treated and/or the lye near surface regions of the implant to be treated are locally heated.

10. Process according to claim 4, characterised in that special biocompatible substances are coupled at least to part regions of the surface regions of the implant exposed previously to a lye.

11. The implant according to claim 1, wherein said animal is a human.

12. The process according to claim 5, wherein temperature of the lye and/or of the implant surfaces to be treated is between 80° C. to 120° C.

13. The process according to claim 9, wherein the local heating is accomplished by pulsed laser radiation.

* * * * *